US010832820B2

(12) United States Patent
Connell, II et al.

(10) Patent No.: US 10,832,820 B2
(45) Date of Patent: Nov. 10, 2020

(54) COGNITIVE PERSONAL HEALTH LIMIT DETECTOR AND TRAINER USING A WEARABLE SMART MOBILE DEVICE

(71) Applicant: International Business Machines Corporation, Armonk, NY (US)

(72) Inventors: Jonathan Hudson Connell, II, Cortlandt Manor, NY (US); Nalini K. Ratha, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 575 days.

(21) Appl. No.: 15/585,402

(22) Filed: May 3, 2017

(65) Prior Publication Data
US 2018/0322255 A1  Nov. 8, 2018

(51) Int. Cl.
*G06Q 30/02*  (2012.01)
*G16H 50/30*  (2018.01)
(Continued)

(52) U.S. Cl.
CPC ............. *G16H 50/30* (2018.01); *G16H 10/60* (2018.01); *G16H 40/67* (2018.01); *G16H 50/20* (2018.01)

(58) Field of Classification Search
CPC . A61B 5/681; A61B 5/02427; A61B 5/02438; H04L 67/12; G16H 50/20;
(Continued)

(56) References Cited

U.S. PATENT DOCUMENTS 5,008,548 A  4/1991  Gat
7,542,878 B2  6/2009  Nanikashvili
(Continued)

FOREIGN PATENT DOCUMENTS

WO  2006001005  1/2006
WO  2012023136  2/2012
WO  2014108851  7/2014

OTHER PUBLICATIONS

Day, M.C., et al., "This is your heart speaking. Call 911", Ergonomics in Design: The Quarterly of Human Factors Applications, Apr. 2012, pp. 1-9, vol. 20, No. 2.
(Continued)

*Primary Examiner* — Maroun P Kanaan
(74) *Attorney, Agent, or Firm* — Fleit Intellectual Property Law; Donna Flores

(57) ABSTRACT

A computer-implemented method, data processor and computer program product determine exposure levels to external stimuli. At least one environmental condition is monitored and an external stimulus event is identified based on the at least one environmental condition. An intensity level of the external stimulus event is determined to exceed a predetermined threshold. An exposure level of the external stimulus is determined by integrating the intensity level over time. At least one human biometric quantity of a user is measured and a personal exposure level limitation is determined for the user based on the measured at least one human biometric quantity. When the exposure level exceeds the personal exposure level limitation, the user is warned of the exposure level. The human biometric quantity is one of: heart rate, blood pressure, body temperature, glucose level, blood oxygen level, muscle activity, electrolyte level, and lactic acid level.

11 Claims, 8 Drawing Sheets

(51) Int. Cl.
*G16H 10/60* (2018.01)
*G16H 40/67* (2018.01)
*G16H 50/20* (2018.01)

(58) Field of Classification Search
CPC ........ G16H 40/67; G16H 10/60; G16H 20/70; G16H 50/30; G06F 1/163; G06F 3/011; G06F 3/013; G06Q 20/40145
See application file for complete search history.

(56) References Cited

U.S. PATENT DOCUMENTS

| | | |
|---|---|---|
| 8,301,232 B2 | 10/2012 | Albert et al. |
| 9,024,271 B2 | 5/2015 | Aslam et al. |
| 9,068,887 B1 | 6/2015 | Bennouri et al. |
| 9,116,045 B2 | 8/2015 | Lian et al. |
| 2009/0224881 A1 | 9/2009 | Koon et al. |
| 2010/0096559 A1 | 4/2010 | Yao et al. |
| 2010/0253509 A1 | 10/2010 | Fu et al. |
| 2014/0188287 A1 | 7/2014 | Sabata |
| 2016/0174912 A1* | 6/2016 | Cronin .................. A61B 5/746 702/19 |
| 2018/0108236 A1* | 4/2018 | Kanukurthy ....... G08B 21/0275 |

OTHER PUBLICATIONS

Jovanov, E., et al., "Patient Monitoring Using Personal Area Networks of Wireless Intelligent Sensors", Biomedical Sciences Instrumentation, Dec. 2001, pp. 1-6, vol. 37.

Mitchell, M., et al., "ContextProvider: Context Awareness for Medical Monitoring Applications", Proceedings of the 33rd Annual International Conference of the IEEE Engineering in Medicine and Biology Society (EMBC), Aug. 30-Sep. 3, 2011, pp. 1-4.

* cited by examiner

COGNITIVE PERSONAL HEALTH LIMIT DETECTOR AND TRAINER USING A WEARABLE SMART MOBILE DEVICE

BACKGROUND

Field of Invention

The present disclosure generally relates to the field of monitoring wearable sensors, and more particularly to collecting, storing and analyzing data obtained from sensors on a person and from other sources.

Description of the Related Art

Mobile wearable devices can detect several health monitoring signals. For example, the wearable devices can detect when the body is starting to react to an external stimulator such as cold during a snow storm, heat (UV) at a beach, pollen in fall and spring, time spent inside a swimming pool, exposure to chemicals, food at a restaurant, sugar level in blood for a diabetic, etc. For a limited time, this exposure to external elements may not cause future sickness; however, the limit is very personal and geared to an individual.

BRIEF SUMMARY

In various embodiments, a computer-implemented method, data processor and computer program product for determining exposure levels to external stimuli are disclosed. At least one environmental condition is monitored and an external stimulus event is identified based on the at least one environmental condition. An intensity level of the external stimulus event is determined to exceed a predetermined threshold. An exposure level of the external stimulus is determined by integrating the intensity level over time. At least one human biometric quantity of a user is measured and a personal exposure level limitation is determined for the user based on the measured at least one human biometric quantity. When the exposure level exceeds the personal exposure level limitation, the user is warned of the exposure level.

BRIEF DESCRIPTION OF THE SEVERAL VIEWS OF THE DRAWINGS

The accompanying figures where like reference numerals refer to identical or functionally similar elements throughout the separate views, and which together with the detailed description below are incorporated in and form part of the specification, serve to further illustrate various examples and to explain various principles and advantages all in accordance with the present invention, in which.

DETAILED DESCRIPTION

Figure 1:
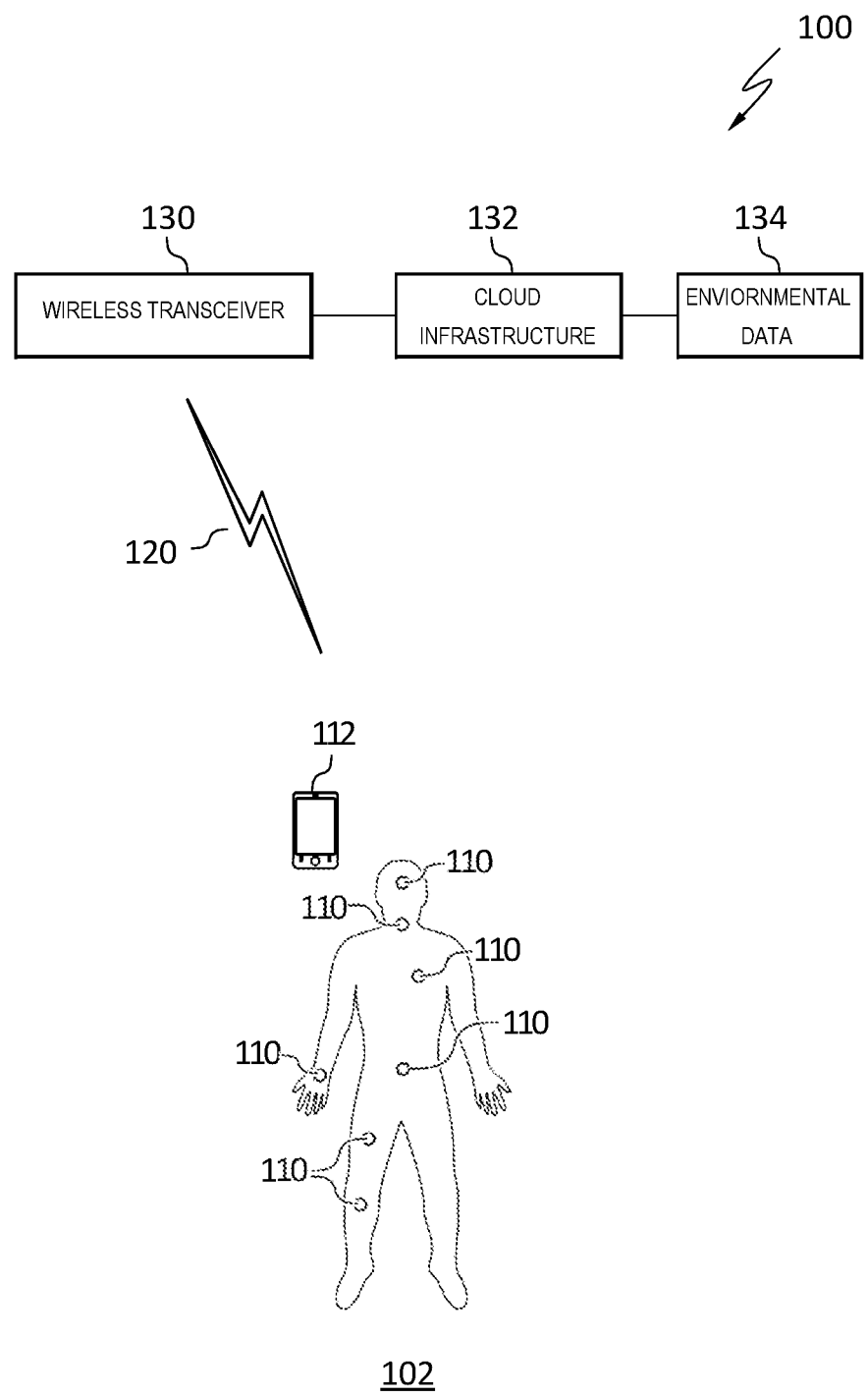
FIG. 1 illustrates a person monitoring environment, in accordance with the present invention.

The below described system and method operate to provide integrated wearable electronics that make up a system of sensors and healthcare monitors that are coupled with one or more interactive sensors, micro-controllers, energy source, or memory storage to provide an integrated and convenient physical monitoring system for a person or animal. In addition, environmental sensors and/or other sources of environmental data (such as thermometers, pollen detectors, ultraviolet (UV) radiation detectors, light sensors, websites that monitor environmental conditions) provide information that, combined with the sensors monitoring personal physical factors, may be used to warn a user of potential, impending dangers that may specifically affect that user.

In one example, micro-subsystems that include sensors can be skin-wearable, placed within wearable articles such as clothing, shoes/sneakers or equivalent, socks, hat, gloves, scarfs, wearable smart tags, watches, articles of jewelry, or the like, are disposed around a person, implanted in the person or otherwise attached to the person. These sensors are able to measure quantities associated with the person. In some examples, all, some, part, or combinations, of the microsystems that include sensors are able to be implanted at various locations of the person. In addition, the sensor may be included as part of a wearable smart mobile device, such as a smart watch, which also includes a processor, memory and transceiver as part of the smart mobile device.

In the following discussion, a sensor is said to be physically coupled to a person if that sensor is attached to the person in any way. Examples of physically coupling a sensor to a person include, but are not limited to, placing a sensor in any type of skin wearable article that is worn by the person, placing a sensor in or on any article worn by or attached to the person, by being implanted into the person in any manner, by any other physical coupling, or by combinations of these. Sensors in some examples are said to be physically coupled to the person at a respective location of the person by being physically coupled to a location, such as at a joint or other location, on or near the person's body.

The sensors that are near a person or physically coupled to the person are able to measure quantities that are be associated with one or more of movement of the person, physiological measurements of the person, biometric measurements used to identify the person, environmental information for the person, data from equipment held by or otherwise used by the person, any suitable measurement, or combinations of these. These sensors in an example are able to interact with a smart phone or other device that communicates with and collects the measurements made by these sensors. In an example, the smart phone or other device is able to provide some processing of the quantities measured by these sensors in order to determine information to present to the person or other interested and authorized individuals. The smart phone or other device is further able to provide communications with other systems. In an example, the smart phone or other device is a communications device that provides data communications to a cloud based computing infrastructure or other server based data processing. In an example, the cloud based infrastructure or other server based data processing performs data analytics and determines information, such as characterizations of measured quantities of physical measurements of the person, suggestions regarding physical activity, feedback, other information related, based on, or derived from the quantities measured by the sensors, or combination of these.

In addition to receiving, collecting and analyzing quantities measured by sensors physically coupled to the person, data characterizing environmental conditions at or near the person are also collected in association with the data provided by sensors characterizing the person's movements. For example, such environmental quantities are able to include, but are not limited to, air temperature, humidity, wind speed, ultraviolet (UV) light exposure, concentrations of particulate matter in the air, other quantities, or combinations of these. Environmental quantities that indicate environmental conditions near the person in some examples are able to be obtained from any suitable source. For example, environmental quantities are able to be measured by sensors physically coupled to the person or that are located near the person. An electronic device, such as a smart phone or other electronic device, that receives data from sensors physically coupled to the person are also able to include sensors to measure environmental quantities. Environmental quantities may also be measured by any sensor suitably close to the person. Data indicating environmental conditions are also able to be received from any other source such as publicly available weather, air quality, other environmental condition data, or combinations of these. Environmental quantities indicating environmental conditions are able to be obtained from any one or more of these sources or any other suitable source. Intensity and exposure levels of these environmental quantities may be measured and determined over time to predict illness in the wearer.

These electronic sensors and one or more communication devices in an example form a system that provides personalized monitoring of a person or animal. Animals for which such monitoring apparatuses can be used include, but are not limited to, pets, racing animals, draft animals, animals involved in performing show routines or other demonstrations, other animals whose physical performance is of interest, or any other animal. In the following discussion, any reference to person is intended to include the body of any type of animal, including humans and other animals such as those listed above. These systems are able to provide one or more of multiple functions, data transmission, data storage, or interaction with one or more various processors that are able to be either local, remote, or both. These systems are able to provide information related to health and/or wellness, are able to record body functions and environmental factors including, but not limited to, temperature, hydration, pulse, blood pressure, movements, rate of movements and location of movements of body relative to one another and the person's environment. These systems are further able to sense muscle changes, fatigue, $O_2$ level in the person's blood, or combinations of these.

The measured characteristics and relative movements of different parts of the person are able to be compared to recorded characteristics or movements of that same person or of others. For example, the recorded or determined movements and other characteristics of a person are able to be compared to prior characteristics or movements that were measured at different times of the person's training or development to characterize the training or development of the person. Further, recorded characteristics or movements are able to be compared to measured or determined characteristics or movements for others, such as professional athletes, trainers, or any other person. Such comparisons to that person's past performance or to characteristics of others is able to be a basis for providing feedback, recommendations, other further information, or combinations of these, for the benefit of the person, pet, or to a caregiver.

Examples of applications for such a system include, but are not limited to, monitoring or characterizing a person's wellness or condition, determining energy consumed by the person, determining hydration of the person, dehydration of the person, body temperature and heart rate of the person, other relevant measurements, or combinations of these. Such systems are able to aid, for example, a personal trainer or rehabilitation specialist for activities such as golf or tennis, general personal fitness, recovery from surgery or injury, recovery from or treatment of a medical condition, recording and tracking the person's improvement and history of development, exposure to heat or cold, exposure to allergens, or any other application.

In an example, the measured data and determined characteristics, trends, recommendations, other information, or combinations of these, are able to be encrypted by any part of the system. For example, one or more sensors are able to encrypt measured data prior to sending the data to a device that is physically coupled to or located near the person. A device physically coupled to or located on the person, such as a smart phone or other personal electronic device, is also able to encrypt data prior to sending that data over a data link to a remote server or cloud based infrastructure. The server or cloud based infrastructure is also able to encrypt data that it processes, or that is produced by processing data received from sensors on a person, in order to provide security for the recorded personal information, determined characteristics, performance tracking, recording and to restrict access to that data to only authorized persons.

Various types of sensors and electronics can be used and combined into a monitoring system. Examples include using electronics that are wearable on a person's skin, embedded in one or more types of clothing or worn articles such as socks, shoes, headbands, or other articles. Motion sensors can determine positions of body parts to which they are physically coupled, and sensors or data processing can track the relative positions of two or more sensors with respect to one another. For example, multiple sensors that determine quantities such as position, speed, velocity, other quantities, or combinations of these can each be placed at locations on a person such as the front of each of a person's foot, the back of each of the person's foot, each of the person's ankles, each of the person's knees, at each of one or more positions on the person's hips, at each of one or more positions on the person's shoulders, at each of one or more positions on the person's elbows, at each of one or more positions on the person's wrists, at each of one or more positions on the person's hands, at each of one or more positions on the person's head, or any one of or combinations of these. In an example, sensors determining quantities associated with sensor location, sensor motion, sensor velocity, other quantities, or combinations of these, are able to be placed at or near various joint locations of the person's or animal's body. For example, sensors such as electrocardiogram (ECG) sensors to measure heart rate, electromyography sensors to measure muscle activity, pulse wave sensors to measure blood pressure, heart sound sensors to study heart activity, electrochemical sensors that detect glucose levels from tear and sweat, electrolyte levels from sweat, lactic acid levels from sweat, any other such sensors, or combinations of these are able to be used to determine and report various data that indicates measured quantities for the person.

Sensors that determine pressure applied to the sensor can detect quantities such as weight and impact when combined with data obtained from sensors determining, for example, one or more of motion, direction of movement, sensor position relative to other sensors, other quantities, or combinations of these. Sensors that monitor electrical resistance can determine ambient humidity, the sweat level on the person, other quantities, or combinations of these. Sensors that capture still images, video images, or both, can be used to detect, for example, movements of ball or equipment such as bats, oars and the like. Determined movements of equipment being used by the person such as balls being caught or thrown, or other equipment can be combined with some or all measurements made by other sensors or with sensors located on, in or otherwise physically coupled to the sports equipment or medical equipment to support improved wellness, healthcare status, quality of an activity, or combinations of these. In general, a piece of equipment being used by a person is able to be any object that is associated with the person's activities. Examples of equipment include, but are not limited to, sports equipment, medical equipment, any other object, or combinations of these. Use of a piece of equipment by a person is able to include, but is not limited to, use of all or part of a piece of equipment. Use of equipment can include, but is not limited to, manipulation of the equipment or object, throwing or swinging of an object associated with the equipment, lifting of an object associated with the equipment, any affect the person may have on an object associated with the equipment, or combinations of these. In general, any measurement or other data characterizing or reflecting movement, use, manipulation of, or other affect on, by the person's activities an object that is all or part of a piece of equipment is referred to as equipment data. Equipment data is able to be measured, determined, otherwise derived, or combinations of these, by sensors within the equipment, sensors external to the equipment, monitoring of the equipment such as by a video capture device, by other techniques, or by combinations of these.

Such measurements, data determinations, or both, are able to be made at any time, such as during exercise, practice, or actual game play. Monitoring such quantities and processing the measured data to determine characteristics for the person is able to be applied to improving performance in various activities, such as personal training for golf, tennis, running, swinging a baseball bat, oar rowing, crew, or any sport. This monitoring, data determination, or both, are also able to aid in monitor progress during treatment for a medical condition or during recovery from a medical procedure such as surgery. In addition, exposure levels and measured human body characteristics may be used to predict likelihood of illness due to environmental conditions.

Using multiple sensors that are able to be physically coupled to the person at selected locations of a person's body, as well as potentially on sports equipment or other equipment used by the person such as medical equipment, is able to support monitoring, characterizing, and determination of exercises and training. Combining these measured quantities with environmental data and equipment data offers a more comprehensive set of data to provide to analysis algorithms Such analysis in some examples is able to be used to support efforts to improve complex physical actions, such as improve a person's posture during sporting activities such as golf by tracking data, communicating that data to a data processor or processors such as in a smart phone, other local device, or other data analysis components such as a cloud based infrastructure. Different levels of analysis in some examples are able to be performed by these various processors in order to determine characteristics and formulate recommendations based on the multiple quantities monitored by the multiple sensors of these comprehensive monitoring systems. The data processor or processors are then able to return such recommendations for further personal training or wellness development, for additional monitoring points to include in the monitoring system during future activities, improvements to exercise, or combinations of these.

In various examples, analysis of the multiple measured quantities and the determination of characteristics are able to be performed by processors located at any suitable location. For example, some processing of measured quantities for a person is able to be performed by processors within a device that is with the person, such as a smart phone or other processor. Some processing is able to be performed by a remote server, such as within a cloud infrastructure, that receives measured quantities, data derived from those measured quantities, or both, from a device with the person.

Data processing used to analyze determined quantities or characteristics is able to include comparisons or other processing based on many diverse sources. For example, a person's measured quantities or characteristics determined by processing or analysis of those determined measured quantities are able to be compared to a set of reference data compiled from any suitable source. For example, deductions or other results are able to be based on comparing measured quantities, or determined characteristics, for a person to any portions of various reference data sets. Examples of reference data sets include large sets of reference data compiled by collecting data from many persons in various demographic groups, from many different types of people participating in similar athletic activities, reference data compiled from any population, or combinations of these. Such data is able to be further presented to skilled persons for analysis, such as to doctors, heath services, other developmental experts, other persons, or combinations of these. These measured quantities and determined characteristics, along with their historical trend as these quantities and characteristics are accumulated over time are able to be used to determine a person's progress and development. Such historical trends are able to assist doctors, health care providers, other wellness professionals, or combinations of these, to determine or detect long term trends in the person's wellness that may benefit from suggested activities.

In an example, such monitoring systems are able to monitor quantities to determine characteristics such as fatigue, dehydration level, wind speed, physical endurance, heart rate, running impact on road, forces on the person's legs and other bones, the person's weight over time versus loss of fluids, body levels of glucose, and body temperature. These data are able to be combined with, for example, one or more types of environmental data, equipment data, other relevant data, or combinations of these. Derived data based on determining trends of quantities and characteristics associated with personal performance and also ambient conditions include aiding a person in identifying conditions when the person does well or when the person has "good days" or "bad days" for speed.

Access to a person's data may be controlled by various techniques. In some examples, sensors measure biometric identification data for the person, such as one or more of fingerprints, retina scans, other biometric identification data, or combinations of these. This biometric identification data is able to be used for any purpose, such as to identify the person in association with stored data to ensure that the data for a particular person was measured for that person, used upon attempts to access data to ensure that person attempting access is the person for whom the data was collected, for any other purpose, or for combinations of these.

FIG. 1 illustrates a person monitoring environment 100, according to an example. The multiple person monitoring environment 100 illustrates a person 102 having a wearable monitoring system that includes multiple wearable sensors 110 that are physically coupled to each person. In various examples, the wearable sensors 110 are able to include one or more of sensors that are within or attached to articles worn by the person, sensors that are attached to the person, sensors that are implanted into the person, sensors that are physically coupled to the person in any manner, or combinations of these. In an example, each wearable sensor 110 measures or determines one or more quantities associated with the person's activity. These wearable sensors 110 are physically coupled at various selected points on the person. In some examples, one or more such wearable sensors are able to measure multiple quantities, such as environmental data, video data, other data, or combinations of these.

The multiple wearable sensors 110 on the person 102 in this example each measure one or more quantities and communicate those quantities to a device 112 that is on or near that person. In some embodiments, the device 112 incorporates at least one sensor 110 as a wearable smart mobile device. In various examples, the wearable sensors 110 are able to encrypt the data that is communicated to the device in order to protect the information associated with the person wearing the wearable sensor 110. For example, the wearable sensors 110 worn by the first person 102 is able to encrypt data indicating quantities measured by that sensor prior to sending that data to the first device 112.

In some examples, the device 112 is able to perform some processing of the data received from the wearable sensors 110. For example, such data is able to be converted as may be useful, some characteristics may be determined from the data received from the sensors, any other processing may be performed, or combinations of these. In addition, data received by or generated within the devices is able to be encrypted for further transmission, storage, other uses, or combinations of these. The devices such as device 112 is also able to store data, such as data received from the wearable sensor 110 or data generated by processing or other means within the device, or both. The device 112 in some examples is also able to receive data from various other sources that are either within or external to the device 112 and that data is able to be stored, further processed, presented to the person 102, otherwise used, or combinations of these.

The device 112 is able to associate measured quantities with a time point associated with the measurement. The time point associated with a measurement in some examples corresponds to the time at which the measurement was made and indicates the time at which the measured quantity existed in, with, or around the person. In some examples, an indication of the time point is stored with the measured quantities, stored with data derived by processing the measured quantities, stored with other relevant data, or stored with combinations of these.

The device 112 is able to associate limits for values of quantities measured by the sensors 110, or for characteristics derived from those measured quantities, and monitor those values relative to those limits. In an example, measured quantities that are within the limits associated with those quantities are reported less frequently than values that fall outside those limits. In some examples, conditions associated with the person 102 are derived by processing within the device 112 to determine, for example, an indication that the person 102 is having a heart attack or has fallen. In some examples, the device 112 sends urgent alerts to identified destinations such as emergency responders, caregivers, parents, custodians, other persons or entities, or combinations of these. In some examples, sensors 110, device 112 or both, are able to have limits associated with their measurements and measured quantities within those limits are able to be defined to be not reported, accumulated and reported with less frequency that values that are not within limits, have a set of processing defined for values that are within limits and another set of processing for values that are not within limits, or any combinations of these.

The device 112 on person 102 is able to exchange data with a cloud infrastructure 132, or other server based processor, over a wireless link 120. The device 112 communicates data in conjunction with a wireless transceiver 130 with the cloud infrastructure to convey measured quantities determined by the wearable sensors 110, data determined by the device 112 by processing or other means, indications of time points associated with the data, or combinations of these.

In addition to receiving data regarding measured quantities from sensors physically coupled to a person 102, the cloud infrastructure 132 in some examples receives environmental data from one or more sources indicated as an environmental data source 134. The environmental data obtained from the environmental data source 134 is environmental data such as is described above. The environmental data is able to be collected at any location such that the data is relevant to the person whose data is being analyzed. For example, air temperature, humidity, UV light levels, and other quantities can be presumed to not vary significantly over some distances. Thus, data obtained from a centrally located environmental monitor may be suitable for incorporation into analyses of data for multiple persons in an area, such as on a golf course, athletic field, and the like. In some examples, the area of relevance for environmental data may be extended to include larger areas such as cities, or any defined area. In some examples, device 112, located near a person 102 is also able to receive environmental data from any suitable local or remote source and incorporate such environmental data into any analysis performed by a processor within such device 112.

Further the device 112 is able to receive data from the cloud infrastructure 132, other server based processor, or from any data source. The device 112 is able to receive data over a wireless link 120 via the illustrated wireless transceiver 130 or any other wireless communications system. The received data is able to be processed, stored, conditioned, displayed to the user, or otherwise utilized by the device. In an example, results determined by processing within the cloud infrastructure 132 based upon quantities measured by the wearable sensors 110 are able to be sent to the device 112, for any purpose, such as presentation to the person 102, for storage to allow later review, for any other purpose, or for combinations of these. In some examples, data sent from the device 112, or sent to the device 112, such as from the cloud infrastructure 132, is able to be encrypted for transmission. The device 112, the cloud infrastructure 132, or both, are also able to encrypt any or all data for storage or other uses in order to protect the data of the person to whom it pertains.

Figure 2:
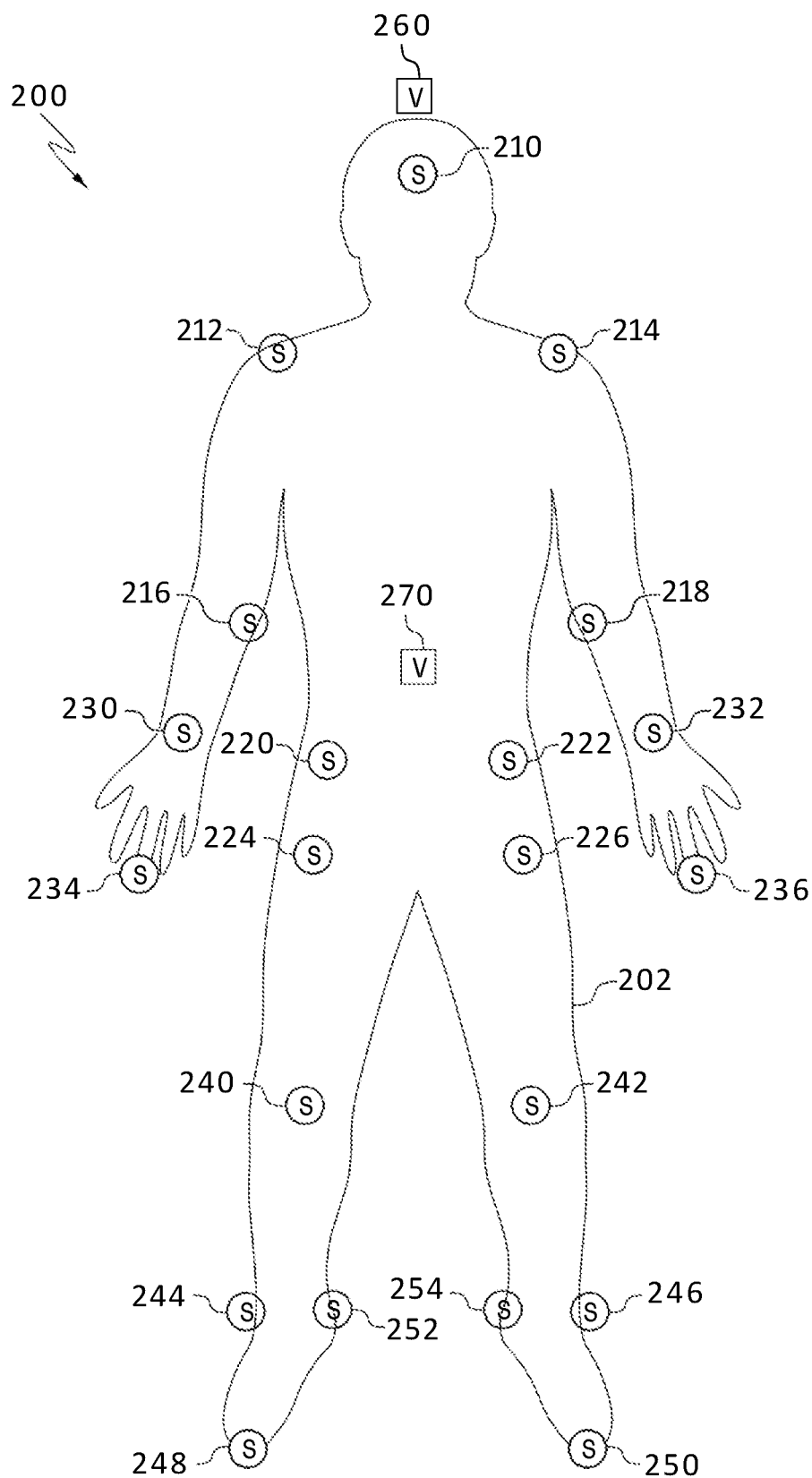
FIG. 2 illustrates a wearable sensor placement configuration, in accordance with the present invention.

FIG. 2 illustrates a wearable sensor placement configuration 200, according to an example. The wearable sensor placement configuration 200 illustrates an example of locations where sensors, such as the wearable sensors 110 discussed above, are physically coupled to a person 202 to implement monitoring of the person's physical performance In some examples, some sensors, or parts of sensors, are able to be physically coupled by any suitable technique, such as by attaching to, implanting in, otherwise physically coupling to, or combinations of these, a person at various locations. In the following discussion, a sensor is said to be placed at a location if it is physically coupled in any manner at a place that is in the vicinity of that location.

The wearable sensor placement configuration 200 depicts a head sensor 210 that is placed on a person's head. The head sensor 210 is able to determine quantities associated with the person's head, such as twisting of the neck as well as movements of the upper body in general that cause the head to move. In general, the head sensor 210 is able to measure and determine one or more of the position of the head with respect to a fixed reference, the position of the head with respect to other sensors on the person 202, a speed and direction of linear movement of the head, a speed and direction of angular movement of the head, ambient wind speed near the head, other relevant quantities, or combinations of these.

The wearable sensor placement configuration 200 depicts a right shoulder sensor 212 and a left shoulder sensor 214 that are placed on each respective shoulder of the person 202. Placing of these and similar sensors may be by any suitable technique, such as direct attachment, placing in clothes or other wearable items, implanting, other physical coupling, or combinations of these. The right shoulder sensor 212 and the left shoulder sensor 214 are able to determine quantities associated with the person's shoulders, such as twisting of the shoulders as well as movements of the upper body in general that cause the shoulders to move. In general, the right shoulder sensor 212 and the left shoulder sensor 214 are able to measure and determine one or more of the position of each respective shoulder in a fixed frame of references, the relative position of each respective shoulder to the other respective shoulder, the relative position of each respective shoulder with respect to other sensors on the persons 202, a speed and direction of linear movement of the respective shoulders with respect to a fixed reference and to other sensors on the person 202, a speed and direction of angular movement of the respective shoulders with respect to a fixed reference and to other sensors on the person 202, ambient wind speed near the shoulders, other relevant quantities, or combinations of these.

The wearable sensor placement configuration 200 depicts a right elbow sensor 216 and a left elbow sensor 218 that are placed on each respective shoulder of the person 202. The right elbow sensor 216 and the left elbow sensor 218 are able to determine quantities associated with the person's elbows that are similar to those described above as being measured or determined for the person's shoulders by the right shoulder sensor 212 and the left shoulder sensor 214. Similar monitoring and determinations are able to be made by other wearable sensors physically coupled at or near various joints of the person 202 such as the right wrist sensor 230 and left wrist sensor 232, the right hand sensor 234 and left hand sensor 236, a right waist sensor 220 and left waist sensor 222, a right hip sensor 224 and left hip sensor 226, a right knee sensor 240 and left knee sensor 242, and also a right foot sensor 248 and a left foot sensor 250.

In some examples, having multiple sensors are able to be placed near a single joint to monitor quantities to allow more detailed analysis of movements during certain processes. An example in the illustrated wearable sensor placement configuration 200 is the use of a right outer ankle sensor 244 and a right inner ankle sensor 252 along with a left outer ankle sensor 246 and a left inner ankle sensor 254. These multiple sensors worn at different locations near a single joint allow more complex movements to be monitored and recorded for analysis.

Some sensors placed on the person are also able to measure or determine biometric identification data. Such biometric identification data is able to include any data that is able to identify the person. Examples of biometric identification data include, but are not limited to, fingerprints, retina scans, measurements of other unique characteristics, or combinations of these. For example, the right hand sensor 234 is able to be placed on the person's fingertip to measure the person's fingerprint. Characterizations of that fingerprint in this example, are biometric identification data that is able to be, for example, used to uniquely identify the person to verify that measured quantities are stored in association with the correct person, used to limit access to data associated with the person to persons with the same biometric identification data, used for any other purpose, or combinations of these.

In addition to the above described wearable sensors, two visual sensors are shown as being worn by the person 202. A head mounted visual sensor 260 and a torso mounted visual sensor 270 are shown as being mounted on the head and torso, respectively, of the person 202. Such visual sensors are able to capture and record images, videos, or other photographic information in a field of view of those sensors. Such images are able to capture, for example, positions and movements of devices used by the person 202, such as bats or cubs swung by the person 202, balls or other objects thrown by the person 202, any other object, or combinations of these. Further, captured visual images or videos captured by the visual sensors of fixed objects may be used to further characterize movements by the person wearing those visual sensors. In various examples, the visual sensors, such as the head mounted visual sensor 260 or torso mounted visual sensor 270, are able to capture one or more portions of light spectrum, including visual light, infrared light, ultraviolet light, any portion of frequencies of electromagnetic radiation, or any combinations of portions of electromagnetic radiation frequencies.

Figure 3:
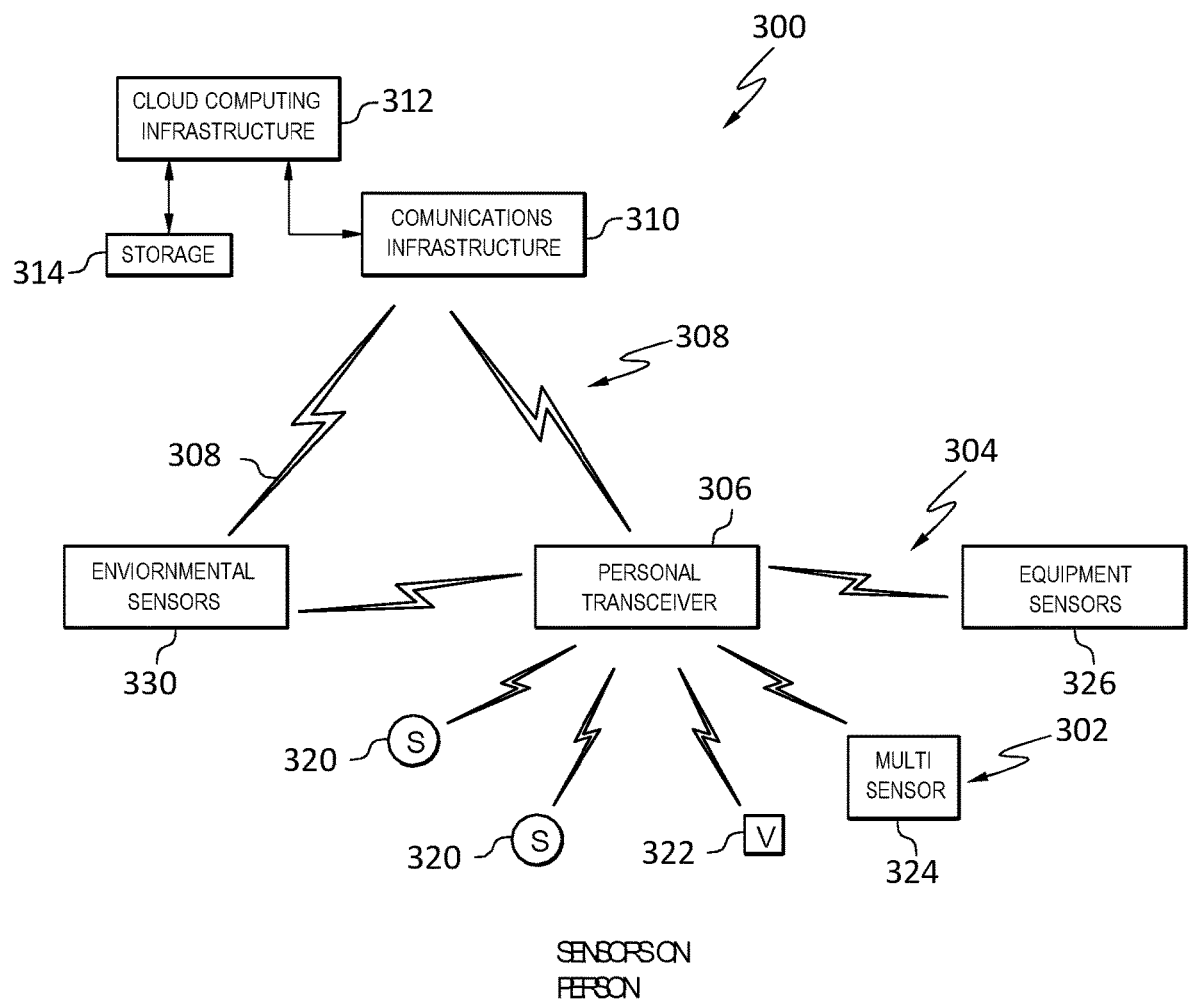
FIG. 3 illustrates a wearable monitoring system interaction diagram, in accordance with the present invention.

FIG. 3 illustrates a wearable monitoring system interaction diagram 300, according to an example. The wearable monitoring system interaction diagram 300 illustrates the interaction and exchange of data between wearable sensors 302, such as are described above with regards to the wearable sensor placement configuration 200, and other components.

The wearable monitoring system interaction diagram 300 depicts a number of wearable sensors including sensors 320 that are in communications with a personal transceiver 306. Personal transceiver 306, in one embodiment, may be included as a component in the device 112 described above. The sensors 320 are examples of the sensors 110 depicted in the multiple person monitoring environment 100 and also described above with regards to the wearable sensor placement configuration 200. These sensors 320 are shown in this example to be in wireless communication with the personal transceiver 306 via wireless data links 304. In various examples, the sensors 320 are able to communicate data with the personal transceiver 306 by any wireless technique, such as via data links conforming to Bluetooth®, Near Field Communication, light based communications, other RF communications, other wireless communications, or combinations of these. In other examples, the sensors 320 are able to communicate with the personal transceiver 306 via wired data links.

The wearable monitoring system interaction diagram 300 also depicts a visual sensor 322 that is also in communications with a personal transceiver 306. Examples of a visual sensor 322 are the head mounted visual sensor 260 and the torso mounted visual sensor 270 describe above. The wearable monitoring system interaction diagram 300 further depicts a multi sensor 324 that is also in communications with a personal transceiver 306. The multi sensor 324 is an example of a sensor that is able to sense different quantities and send indications of those quantities to the personal transceiver 306. In an example, the sensors 320, the visual sensor 322, and the multi sensor 324 are able to encrypt data for transmission to the personal transceiver 306.

One or more of sensor 320 or multi sensor 324 is able to determine various quantities related to conditions of the person or related to ambient conditions. For example, such sensors are able to measure pulse rate, blood pressure, $O_2$ levels in the person's blood, any other quantity, or combinations of these.

Equipment sensors 326 are further able to be used in some examples to determine or otherwise derive movements or other characteristics of equipment used by the person. For example, sensors within a ball, bat, medical equipment, other device used by or affected by a person, are able to measure characteristics of affects and effects on that device. Further, equipment sensors 326 in some examples are able to include sensors that are external to the equipment, such as video equipment or other sensors, are able to also characterize usage of some or all of a piece of equipment being used by a person. Such data are provided by equipment sensors 326 is able to be provided to the personal transceiver 306 via any suitable technique, such as a wireless data link 304, and combined with data from other sensors in any suitable manner.

Environmental sensors 330 in some examples measure environmental data near the person and report such data by any technique. For example, environmental data such as air temperature, humidity, other environmental data quantities, or combinations of these, are able to be obtained by the environmental sensors 330. The environmental sensors 330 in some examples are able to communicate with the personal transceiver 306 via a wireless data link 304 and report some or all environmental data to the personal transceiver 306. The personal transceiver 306 is then able to incorporate such environmental data into analyses performed by a processor within the personal transceiver 306, or report the received environmental data with measurements received from other sensors.

In some examples, the personal transceiver 306 is also able to include sensors that determine quantities that can be combined with data indicating quantities determined by sensors worn on the person. For example, sensors determining environmental data at a location proximate to the person, such as measurements including one or more of ambient temperature, humidity, atmospheric pressure, other environmental quantities or conditions, or combinations of these, can be included in the personal transceiver. Additionally, visual sensors such as image capture, video capture, other visual capture capabilities, or combinations of these can be included in the personal transceiver 306. Such personal transceiver mounted visual sensors can be used to, for example, capture images or videos of the person while the person is performing actions of interest, capture images or videos of equipment held or otherwise manipulated or used by the person such as a bat being swung or a ball being thrown, or any other visual information.

The wearable monitoring system interaction diagram 300 illustrates wireless connections between sensors and the personal transceiver 306. In further examples, any suitable communications link is able to be used to convey data between the sensors and the personal transceiver 306. In some further examples, sensors are able to accumulate data and transfer data to any destination over any suitable link, such as over one or more wireless links, wired data links, other links, or combinations of these.

The personal transceiver 306 is able to communicate with a communications infrastructure 310 in order to exchange data with a cloud computing infrastructure 312. In an example, the personal transceiver 306 sends data indicating measured quantities determined by the sensors 320, visual sensor 322, and multi sensor 324 to the cloud computing infrastructure 312. In some examples, the environmental sensors 330 are able to transmit environmental data directly to the communications infrastructure 310 for reporting to the cloud computing infrastructure 312.

The data transmitted from the personal transceiver 306 to the communications infrastructure 310, and on to the cloud computing infrastructure 312, is able to be encrypted. This encryption is able to be performed by various components, such as by the sensor, e.g., sensor 320, visual sensor 322, or multi sensor 324, prior to sending the data to the personal transceiver 306, or the encryption is able to be performed by the personal transceiver 306 prior to transmission. The communications infrastructure 310 in various examples is able to support communications in one or both directions over the wireless data link 308 in any suitable form, such as over wide area cellular data communications networks, over Wi-Fi® networks, over any suitable communications using any combination of wired or wireless networks, or over combinations of these. In further examples, the personal transceiver 306 is able to communicate via a wired communications channel conveying either data that has been accumulated within the personal transceiver 306, data being received or processed within the personal transceiver 306, any data within the personal transceiver 306, or combinations of these.

In some examples, the personal transceiver 306 is able to accumulate measured quantities and other data without transmitting that data until certain criteria are reached. For example, an amount of data may be specified to be accumulated prior to transmission. Further conditions may be specified such that anomalous or data meeting other criteria is reported sooner. Transmitting accumulated data in some examples conserves energy used to transmit the data, while setting other criteria for earlier transmission ensures more interesting data is sent without unnecessary delay.

The personal transceiver 306 in some examples is able to include processing capabilities to perform analysis of measure quantities in order to derive characterizations or other information to provide to the person or to other processors. In some examples, the personal transceiver 306 is able to include a cognitive processor or cognitive computer to analyze data in according to any suitable technique. Examples of cognitive processors or cognitive computers include, but are not limited to, processors that perform processing to implement concepts such as artificial intelligence, machine learning algorithms, or any other suitable techniques. In some examples, the personal transceiver 306 is able to compare measured quantities or derived characteristics to expected values in order to identify anomalous condition. For example, measured data is able to be analyzed to determine if a person has fell, had a heart attack, is undergoing another anomalous situation, or combinations of these. Sending notifications of data that may indicate such conditions notifies others, such as emergency responders, caretakers, others, or combinations of these, of situations that may need attention.

Processing within the cloud computing infrastructure 312 analyses the data received from the personal transceiver 306, and produces results to report to the person associated with the personal transceiver 306. The cloud computing infrastructure 312 is an example of a remote processor to which data is sent from the personal transceiver 306. In some examples, the cloud computing infrastructure 312 is able to include cognitive computers or cognitive processors to perform some functions as is described above. The cloud computing infrastructure 312 is able to store received data indicating measured quantities, store characteristics determined from that received data, store, in association with the data, time points that are associated with that data, store other data, or combinations of these, into a storage 314. The stored data is able to be encrypted in order to, for example, protect the privacy of the person. Alternatively, some or all of the received data, determined characteristics, other data, or any combination of these, are able to be stored in unencrypted form.

Figure 4:
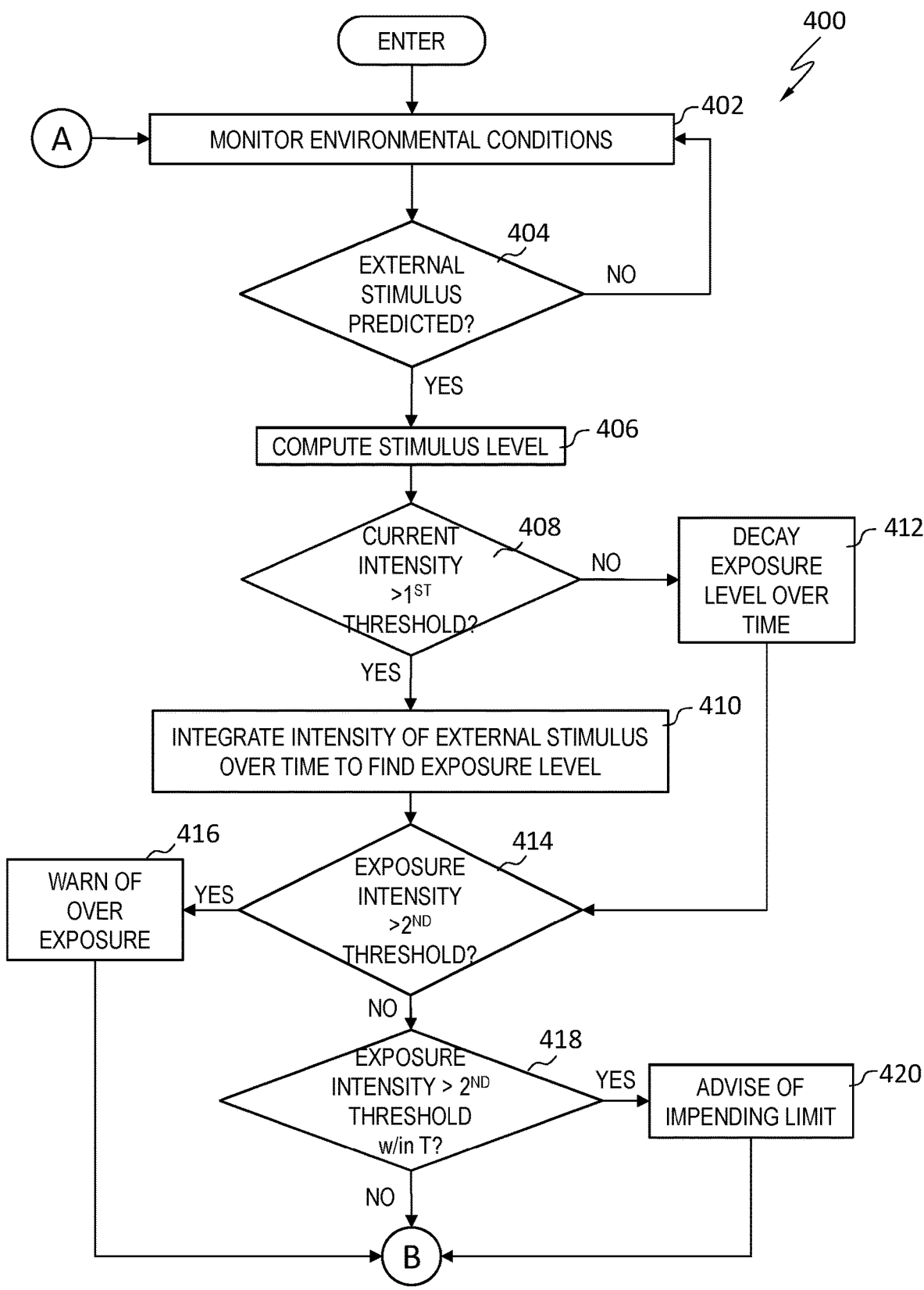
FIG. 4 illustrates a first portion of an environmental exposure monitoring and warning process, in accordance with the present invention.
Figure 5:
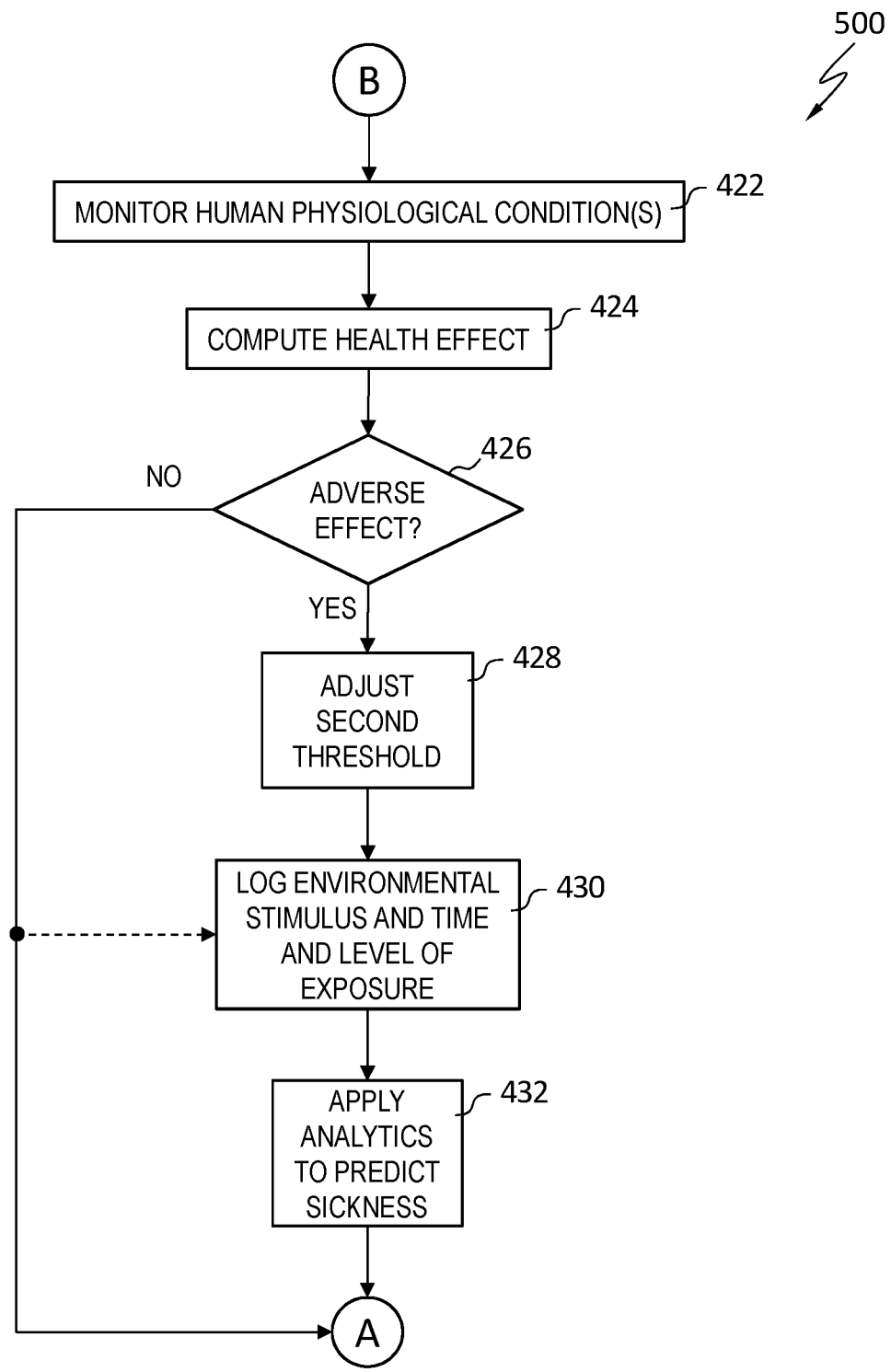
FIG. 5 illustrates a second portion of the environmental exposure monitoring and warning process of FIG. 4, in accordance with the present invention.

FIGS. 4 and 5 illustrate an environmental exposure monitoring and warning process 400, according to one embodiment of the present invention. The environmental exposure monitoring and warning process 400, in one example, is performed by a processor within the personal transceiver 306, as is described above, in conjunction with other elements of the wearable monitoring system interaction diagram 300. In further examples, some of this processing is able to be performed by processors within the personal sensors 320, 322, or 324 or the environmental sensors 330 themselves prior to reporting measured data to the personal transceiver 306.

The environmental exposure monitoring and warning process 400 begins, at step 402, by monitoring environmental conditions. Environmental data, such as temperature, humidity, particulate levels (e.g., pollen count, smoke or other pollution), sunlight or ultraviolet radiation, other environmental data, or combinations of these are also able to be determined as measured quantities. In some examples, environmental data, such as pollen count, barometric pressure, temperature, humidity, etc., may be received or retrieved from an external source, such as via the Internet or other data source. In some examples, the time of these measurements is determined and associated with the measured quantity. The time of measurement may be retained with and sent along with the measured quantity in some examples so as to be available for subsequent processing. An environmental stimulus may be a set of all available monitored conditions or a subset of the available monitored conditions. Potential stimuli may be specified by the user, a health service provider or other entity. Default stimuli may be preset with the system.

At step 404, the intensity level of the environmental stimulus is computed. The intensity level may be computed by measuring levels using the environmental sensors 330, (e.g., temperature readings from a thermometer) or by receiving geographical environmental data from a remote site, such as receiving local temperature data via the Internet. A determination is made, at step 406, as to whether any measured environmental stimulus or combination of stimuli are outside of predetermined limits (e.g., intensity level is above a first predetermined threshold.) This first threshold may be a coarse indication of the presence of a potential hazardous situation. For example, if the potential hazardous situation is exposure to ultraviolet radiation, the first threshold may simply be whether it is night or day. In this example, the intensity level may be computed by measuring UV levels using a UV sensor, measuring luminous intensity using a light sensor, or at a very coarse level, by knowing the time the sun rises/sets and the local weather forecast (e.g., sunny, cloudy, mostly cloudy, etc.). In another example, for pollen count, the first threshold may be the determination of a certain level of particulate in the air using an instrument such as a particle counter or, alternatively, simply being notified from an external data source that allergy season has begun. The first threshold may also have a time consideration such that the intensity remains at a certain level for a predetermined period of time (e.g., pollen level exceeds 3 particles/billion for 5 days in a row).

If the stimulus intensity level exceeds the first threshold, at step 408, the intensity level of the environmental stimulus is integrated over time, at step 410, to find an exposure level. For example, when determining UV radiation exposure, UV radiation may be measured at regular intervals over the course of a day, week, etc. As long as the measured intensity is above the first threshold, the prolonged accumulated exposure is increasing, thus the overall exposure intensity level is increasing. By integrating the intensity level over time, a complete view of the effects of the accumulated exposure may be analyzed. However, if the user moves into a shaded area or building, or if the sun sets, the effects of the exposure may be stalled or counteracted (i.e. the user's immune system may allow the user to begin healing from the exposure). Therefore, if the stimulus intensity level does not exceed the first threshold, at step 408, the overall exposure level is decayed over time, at step 412. For example, the exposure intensity level may be decayed a certain set amount or percentage of an amount for every predetermined amount of time for which the stimulus intensity is below the first threshold level.

The decay function depends on the biological process involved. For instance, for sun exposure, the amount of inflammation might depend directly on the number of UV photons received. Once tissue repair processes are started, this exposure might be remedied by a fixed rate of decrease over time. For example, after 30 minutes of intensive sun, the cumulative damage might be 30 (in arbitrary units). The repair process might occur at a rate of 10 per hour, so after 3 hours in the shade, the integral of exposure goes to zero. That is, $V = V_0 - k \cdot t$ where V is the accumulated stimulus, $V_0$ is its peak value, t is the elapsed recovery time, and k is the recovery rate. Here V would never decay beyond zero.

For other environmental conditions, such as low temperature exposure, the recovery process might be non-linear. For example, if bare arms are exposed to humid 40 degree still air for an hour, this exposure level might result in a chilling of 30 (in arbitrary units). In this case, the recovery process might be governed by thermal diffusion back into the tissue, which is dependent on the temperature differential and thickness of the arm. Here the exposure integral V would be decayed as $V = V_0 * e^{(-t/T)}$ where $V_0$ is its initial value, t is the elapsed time, and T is a suitable time constant. So, in this example, if T is 5 minutes, the initial chill of 30 will have decayed to 1.5 (5% of its peak) over the course of 15 minutes.

Returning to FIG. 4, if it is determined, at step 414, that the overall exposure intensity level is greater than a second predetermined threshold, the process warns the user, at step 416, that the environmental conditions have exceeded a level that has been determined to cause adverse effects. In other words, the user has been exposed to the environmental condition to the point where the user may be concerned about the effects of the exposure. The value of the second predetermined threshold may be customized for a specific user and adjusted in response to an adverse effect for the user, as described below.

If the overall exposure intensity level is determined, at step 414, not to be greater than the second predetermined threshold, the process predicts, at step 418, whether the overall exposure level will be greater than the second predetermined threshold within a given period of time (T). In other words, given the current integrated exposure level and the current environmental stimulus level, will the overall integrated exposure level reach the second threshold within the next T units of time (e.g., minutes, hours, days, etc.). If the second threshold is predicted to be reached within time T, the process warns the user of the potential impending exposure limit, at step 420, so that the user may implement preventative measures (e.g., apply sunscreen, seek shelter, take medication, etc.).

At step 422, human physiological conditions are monitored to calculate the health effects resulting from the exposure to the environmental stimulus, at step 424. For example, the external skin temperature may be measured to determine UV radiation exposure. In another example, exposure to a known allergen may be monitored by identifying an act of sneezing and sneezing frequency (e.g., using an accelerometer or other motion sensor), measuring histamine levels in the blood, or measuring a combination of indicators. Effects of exposure to cold temperature may be monitored by measuring skin temperature, detecting shivering (e.g., using an accelerometer or other motion sensor), determining decreased exterior blood flow (e.g., using reflectometry data), or any combination of measurements.

At step 426, the process determines whether an adverse outcome has been detected. An adverse outcome may occur when one or more of the human biometric measurements is outside of a previously determined safe range (e.g., heart rate, blood pressure, blood sugar, blood oxygen or body temperature too high or too low, etc.) or when the person indicates that there is a problem (i.e. the person sends an indication of a problem, such as pushing a button or delivering a voice command) A person may indicate a problem when he/she feels pain, excessive heat or coldness, exhaustion, tiredness, racing heart, etc., that exceeds that person's personal limitations or comfort.

If an adverse outcome is detected, at step 426, an adjustment is made to the second predetermined threshold, at step 428, which is intended to provide adequate warning time to enable the user to determine when he/she is approaching a personal exposure level limitation for exposure to a given external stimulus. Details associated with the environmental stimulus and the user's response, including time and intensity level of exposure, type of environmental stimulus, biometric measurements, etc., are logged at step 430. A notification may be sent to the personal transceiver 306 to warn the user that their personal exposure level limitation has been changed due to an adverse event. The notification may include details describing the adverse outcome, including but not limited to, the duration of the event, the exposure level of the environmental stimulus, the intensity level of the environmental stimulus when the adverse event occurred, the characteristic being monitored and corresponding measurement value that triggered the adverse outcome, instructions or contact information for receiving help, etc. The notification may provide instructions for how to end the current external stimulus (e.g., if the external stimulus is running, the notification may advise to stop immediate exertion; if the external stimulus is a cold temperature, the notification may advise to seek shelter, etc.). It should be noted, in cases where the personal transceiver 306 is a component of a wireless device 102, the notification may not be transmitted, but merely displayed to the user upon a display screen.

Analytics are applied using the logged information to predict whether the person is at increased risk of becoming ill due to contact with the environmental stimulus and the user is notified of possible preventative action to take, at step 432. For example, if the person has been exposed to a cold temperature for an extended period of time, the person may be at increased risk of contracting a cold and may want to begin taking extra vitamin C.

The process will continue to monitor the environmental conditions that triggered the external stimulus, at step 402, until the environmental stimulus intensity level has fallen a certain amount below the first predetermined threshold for a predetermined period of time or the process is manually stopped.

Data indicating the measured biometric quantities, environmental data, intensity levels, exposure levels, events and event durations, etc. that are to reported may be encrypted in one example. This encryption is able to be performed in various examples at other stages of the process, such as by the sensor determining the measured quantity, or this encryption is able to be performed after the quantity is measured by another component, such as the personal transceiver 306 described above. In some alternative examples, the data is able to not be encrypted at this stage or in further examples at any stage.

The encrypted data in one example is transmitted to a cloud computing infrastructure. In an example, with reference to the wearable monitoring system interaction diagram 300 described above, the personal transceiver 306 transmits the encrypted data via a wireless data link 308 to a communications infrastructure 310. Transmission over the wireless data link 308 is able to be in any suitable form, such as over a wide area cellular data communications network, over a Wi-Fi® network, over any suitable wireless network, or over combinations of these. In alternative examples, encrypted or unencrypted data is able to be transmitted to any remote server, such as a server in a cloud based infrastructure, over any suitable channel that includes only wired connections, only wireless connections, or any combination of wired and wireless connections. The environmental exposure monitoring and warning process 400 then returns to determining, at 402, measured quantities for the person and continues with the above described processing.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 5, illustrative cloud computing environment 502 is depicted. As shown, cloud computing environment 502 comprises one or more cloud computing nodes 520 with which local computing devices used by cloud consumers, such as, for example, personal digital assistant (PDA) or cellular telephone 504, desktop computer 506, laptop computer 508, and/or automobile computer system 510 may communicate. Nodes 520 may communicate with one another. They may be grouped (not shown) physically or virtually, in one or more networks, such as Private, Community, Public, or Hybrid clouds as described hereinabove, or a combination thereof. This allows cloud computing environment 502 to offer infrastructure, platforms and/or software as services for which a cloud consumer does not need to maintain resources on a local computing device. It is understood that the types of computing devices 504-510 shown in FIG. 5 are intended to be illustrative only and that computing nodes 520 and cloud computing environment 502 can communicate with any type of computerized device over any type of network and/or network addressable connection (e.g., using a web browser).

Figure 6:
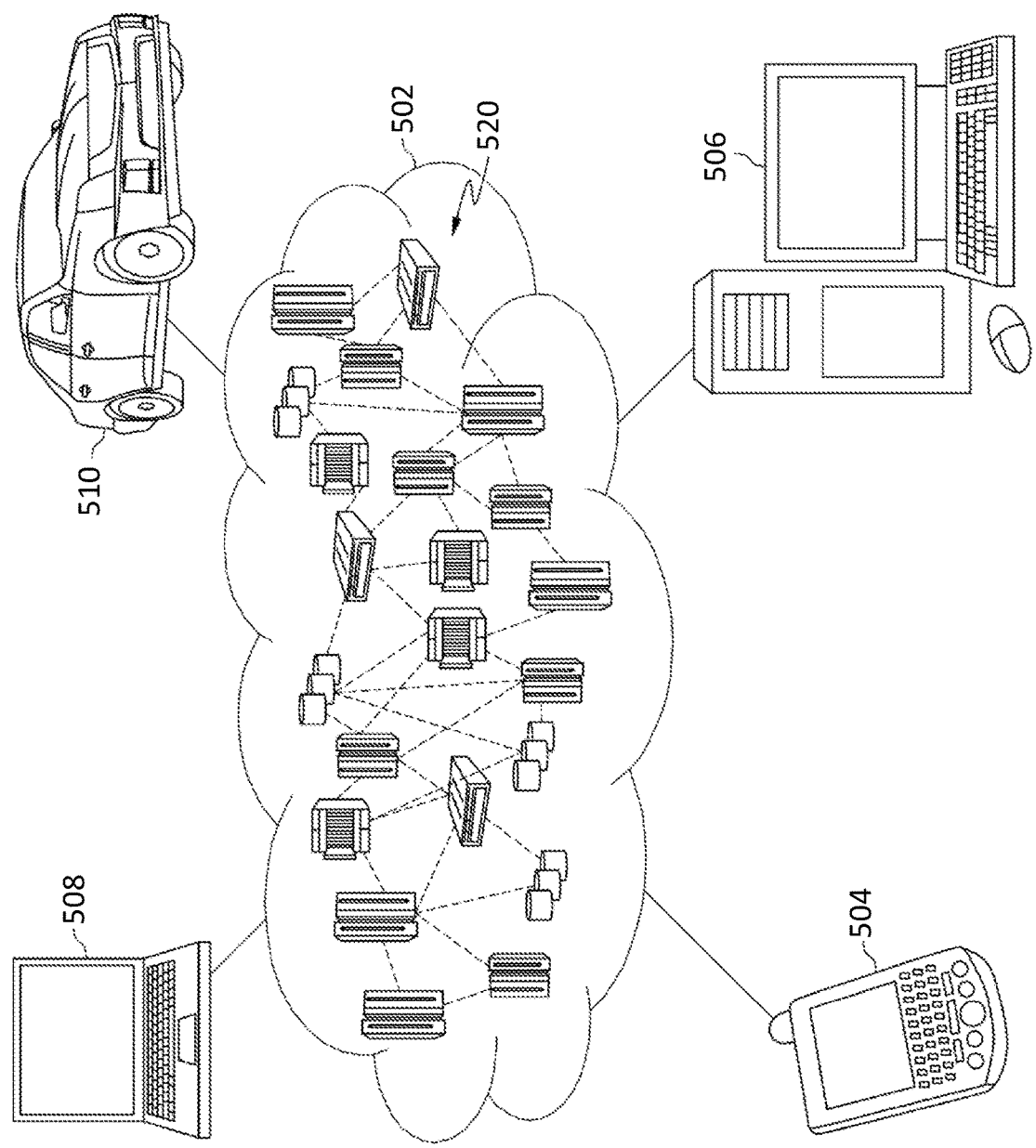
FIG. 6 depicts a cloud computing environment, in accordance with the present invention.

Referring now to FIG. 6, a set of functional abstraction layers provided by cloud computing environment 502 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 602 includes hardware and software components. Examples of hardware components include: mainframes 610; RISC (Reduced Instruction Set Computer) architecture based servers 612; servers 614; blade servers 616; storage devices 618; and networks and networking components 620. In some embodiments, software components include network application server software 622 and database software 624.

Virtualization layer 604 provides an abstraction layer from which the following examples of virtual entities may be provided: virtual servers 630; virtual storage 632; virtual networks 634, including virtual private networks; virtual applications and operating systems 636; and virtual clients 638.

In one example, management layer 606 may provide the functions described below. Resource provisioning 640 provides dynamic procurement of computing resources and other resources that are utilized to perform tasks within the cloud computing environment. Metering and Pricing 642 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 644 provides access to the cloud computing environment for consumers and system administrators. Service level management 646 provides cloud computing resource allocation and management such that required service levels are met. Service Level Agreement (SLA) planning and fulfillment 648 provide pre-arrangement for, and procurement of, cloud computing resources for which a future requirement is anticipated in accordance with an SLA.

Workloads layer 608 provides examples of functionality for which the cloud computing environment may be utilized. Examples of workloads and functions which may be provided from this layer include: mapping and navigation 650; software development and lifecycle management 652; virtual classroom education delivery 654; data analytics processing 656; transaction processing 658; and reported data analysis 660.

Information Processing System

Figure 7:
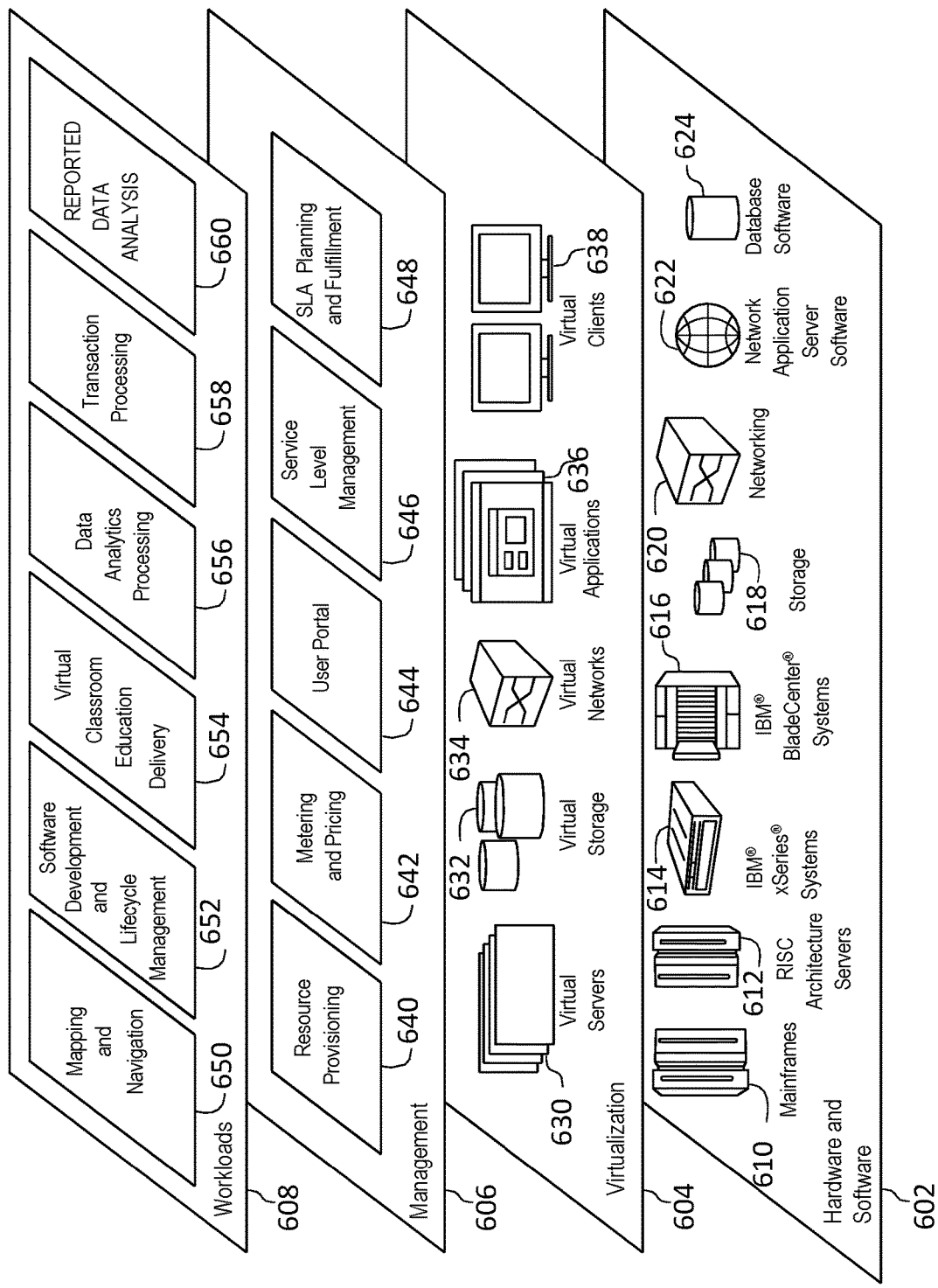
FIG. 7 depicts abstraction model layers according to an embodiment of the present invention.
Figure 8:
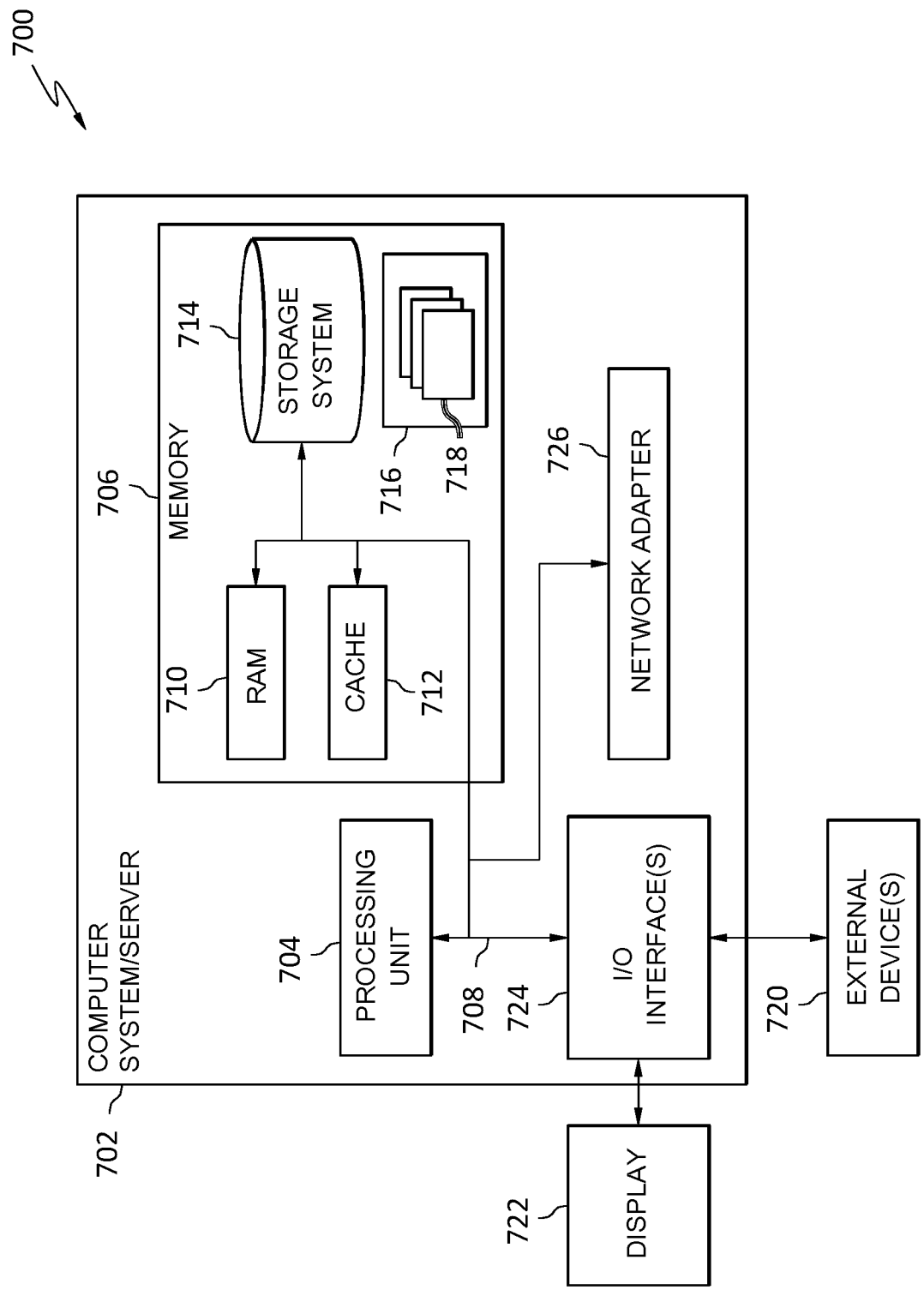
FIG. 8 is a block diagram illustrating one example of an information processing system, in accordance with the present invention.

Referring now to FIG. 7, this figure is a block diagram illustrating an information processing system that can be utilized in various examples of the present disclosure. The information processing system 702 is based upon a suitably configured processing system configured to implement one or more embodiments of the present disclosure. Any suitably configured processing system can be used as the information processing system 702 in embodiments of the present disclosure. In another embodiment, the information processing system 702 is a special purpose information processing system configured to perform one or more embodiments discussed above. The components of the information processing system 702 can include, but are not limited to, one or more processors or processing units 704, a system memory 706, and a bus 708 that couples various system components including the system memory 706 to the processor 704.

The bus 708 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The system memory 706 can also include computer system readable media in the form of volatile memory, such as random access memory (RAM) 710 and/or cache memory 712. The information processing system 702 can further include other removable/non-removable, volatile/non-volatile computer system storage media. By way of example only, a storage system 714 can be provided for reading from and writing to a non-removable or removable, non-volatile media such as one or more solid state disks and/or magnetic media (typically called a "hard drive"). A magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 708 by one or more data media interfaces. The memory 706 can include at least one program product having a set of program modules that are configured to carry out the functions of various examples described above.

Program/utility 716, having a set of program modules 718, may be stored in memory 806 by way of example, and not limitation, as well as an operating system, one or more application programs, other program modules, and program data. Each of the operating system, one or more application programs, other program modules, and program data or some combination thereof, may include an implementation of a networking environment. Program modules 718 generally carry out the functions and/or methodologies of the above described processes and systems.

The information processing system 702 can also communicate with one or more external devices 720 such as a keyboard, a pointing device, a display 722, and the like. The information processing system 702 is further able to communicate with one or more devices that enable a user to interact with the information processing system 702; and/or any devices (e.g., network card, modem, etc.) that enable computer system/server 702 to communicate with one or more other computing devices. Such communication can occur via I/O interfaces 724. Still yet, the information processing system 702 can communicate with one or more networks such as a local area network (LAN), a general wide area network (WAN), and/or a public network (e.g., the Internet) via network adapter 726. As depicted, the network adapter 726 communicates with the other components of information processing system 702 via the bus 708. Other hardware and/or software components can also be used in conjunction with the information processing system 702. Examples include, but are not limited to: microcode, device drivers, redundant processing units, external disk drive arrays, RAID systems, tape drives, and data archival storage systems.

Non-Limiting Examples

As will be appreciated by one skilled in the art, aspects of the present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), a phase change memory (PCM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer-implemented method comprising:
monitoring at least one environmental condition;
identifying an external stimulus event based on the at least one environmental condition;
determining an intensity level of the external stimulus event;
responsive to determining that the intensity level of the external stimulus exceeds a first predetermined threshold:
determining a cumulative exposure level of the external stimulus by integrating the intensity level over time;

measuring at least one human biometric quantity of a user associated with an electronic device;
determining a personal exposure level limitation for the user based on the measured at least one human biometric quantity;
predicting a time when the exposure level will exceed the personal exposure level limitation;
send a notification to the electronic device associated with the user notifying the user of the exposure level at a time preceding the time when the exposure level will exceed the personal exposure level limitation;
detecting an adverse outcome has occurred; and
responsive to detecting the adverse outcome has occurred, adjusting the personal exposure level limitation closer to the predetermined threshold; and
responsive to determining the cumulative exposure level exceeds the personal exposure level limitation for the user, sending a warning to the electronic device associated with the user notifying of the exposure level; and
responsive to determining that the intensity level of the external stimulus does not exceed the first predetermined threshold, decaying the cumulative exposure level of the external stimulus to account for healing effects of the user's body.

2. The method of claim 1, wherein the at least one human biometric quantity is selected from a group consisting of: heart rate, blood pressure, body temperature, glucose level, blood oxygen level, muscle activity, electrolyte level, and lactic acid level.

3. The method of claim 1, wherein detecting the adverse outcome has occurred comprises receiving an indication from the user.

4. The method of claim 1, wherein detecting the adverse outcome has occurred comprises determining at least one human biometric quantity is outside a safe range.

5. The method of claim 1, further comprising:
logging information regarding the external stimulus event; and
applying analytics to the information regarding the external stimulus event to predict an illness of the user.

6. A data processor, comprising:
a data receiver that, when operating:
receives at least one environmental condition; and
receives, from a wearable sensor, at least one human biometric quantity of a user associated with an electronic device;
a data analyzer that, when operating:
identifies an external stimulus event based on the at least one environmental condition;
determines an intensity level of the external stimulus;
responsive to determining that the intensity level of the external stimulus exceeds a first predetermined threshold:
determines a cumulative exposure level of the external stimulus by integrating the intensity level over time;
determines a personal exposure level limitation for the user based on the received at least one human biometric quantity;
predicts a time when the exposure level will exceed the personal exposure level limitation;
sends a notification to the electronic device associated with the user notifying the user of the exposure level at a time preceding the time when the exposure level will exceed the personal exposure level limitation;
detects an adverse outcome has occurred;
responsive to detecting the adverse outcome has occurred, adjusts the personal exposure level limitation closer to the predetermined threshold; and
responsive to determining the cumulative exposure level exceeds the personal exposure level limitation for the user, sends a warning to the electronic device associated with the user notifying of the exposure level; and
responsive to determining that the intensity level of the external stimulus does not exceed the predetermined threshold, decays the cumulative exposure level of the external stimulus to account for healing effects of the user's body.

7. The data processor of claim 6, wherein the data analyzer, when operating, further selects the at least one human biometric quantity a group consisting of: heart rate, blood pressure, body temperature, glucose level, blood oxygen level, muscle activity, electrolyte level, and lactic acid level.

8. The data processor of claim 6, wherein the data analyzer, when operating, further:
predicts a time when the exposure level will exceed the predetermined threshold; and
notifies the user of the exposure level at a time preceding the time when the exposure level will exceed the predetermined threshold.

9. The data processor of claim 6, wherein detecting the adverse outcome has occurred comprises determining at least one human biometric quantity is outside a safe range.

10. The data processor of claim 6, wherein the data analyzer, when operating, further
logs information regarding the external stimulus event; and
applies analytics to the information regarding the external stimulus event to predict an illness of the user.

11. A computer program product for determining exposure levels to external stimuli, the computer program product comprising a non-transitory computer readable storage medium having program instructions embodied therewith, the program instructions executable by a processing circuit to cause the processing circuit to:
monitor at least one environmental condition;
identify an external stimulus event based on the at least one environmental condition;
determine an intensity level of the external stimulus event;
responsive to determining that the intensity level of the external stimulus exceeds a first predetermined threshold:
determine a cumulative exposure level of the external stimulus by integrating the intensity level over time;
measure at least one human biometric quantity of a user associated with an electronic device;
determine a personal exposure level limitation for the user based on the measured at least one human biometric quantity;
predict a time when the exposure level will exceed the personal exposure level limitation;
send a notification to the electronic device associated with the user notifying the user of the exposure level at a time preceding the time when the exposure level will exceed the personal exposure level limitation;
detect an adverse outcome has occurred;

responsive to detecting the adverse outcome has occurred, adjust the personal exposure level limitation closer to the predetermined threshold; and responsive to determining the cumulative exposure level exceeds the personal exposure level limitation for the user, send a warning to the electronic device associated with the user notifying of the exposure level; and responsive to determining that the intensity level of the external stimulus does not exceed the first predetermined threshold, decay the cumulative exposure level of the external stimulus to account for healing effects of the user's body.

* * * * *